United States Patent [19]

Kruse et al.

[11] Patent Number: 4,835,318
[45] Date of Patent: May 30, 1989

[54] PROCESS FOR THE PREPARATION OF ARYL PERFLUOROALKYL KETONES

[75] Inventors: Alfred Kruse, Kelkheim; Günter Siegemund, Hofheim am Taunus; Klaus Schlich, Remagen; Ingo Ruppert, deceased, late of Bonn, all of Fed. Rep. of Germany, by Carl H. Schroeder, Administrator

[73] Assignee: Hoechst Aktiengesellschaft, Frankfurt, Fed. Rep. of Germany

[21] Appl. No.: 225,548

[22] Filed: Jul. 28, 1988

[30] Foreign Application Priority Data

Jul. 29, 1987 [DE] Fed. Rep. of Germany ....... 3725126

[51] Int. Cl.$^4$ ............................................. C07C 45/45
[52] U.S. Cl. .................... 568/319; 568/322; 568/323
[58] Field of Search ....................... 568/319, 322, 323

[56] References Cited

U.S. PATENT DOCUMENTS 4,546,184 10/1985 Baucom .............................. 568/323

OTHER PUBLICATIONS

Ang et al., Chem. Abst; vol. 69, #87,128u (1968).
Villieras et al., Chem. Abst, vol. 74, #111,491h (1971).
Castro et al., Chem. Abst., vol. 75, #129,307h (1971).
D. J. Burton et al., "Fluoride Ion Catalyzed Isomerization of 2-Aryl-F-Butenes", J. Fluorine Chem. 18, 323-329 (1981).
N. Ishikawa et al., *Bull. Chem. Soc. Japan,* 48, 1339-1340 (1975).
K. Dishart et al., J. Amer. Chem. Soc., 78, 2268-2270 (1956).
L. Chen et al., *J. Fluorine Chem.* 18, 117-129 (1981).
W. Hull, Tetrahedron 42, 547-552 (1986).

Primary Examiner—James H. Reamer

[57] ABSTRACT

A process for the preparation of arylperfluoroalkyl ketones of the general formula I

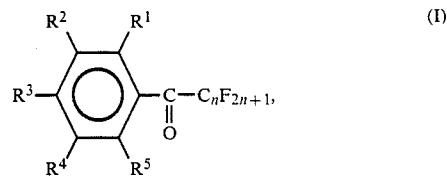

wherein $R^1$ and $R^5$ represent at least one of the substituents hydrogen, halogen, alkyl, alkoxy, alkylthio and perfluorinated alkyl, each having from 1 to 6 carbon atoms and n is an integer from 1 to 6, which comprises reacting an aryl carbonyl compound having the general formula II

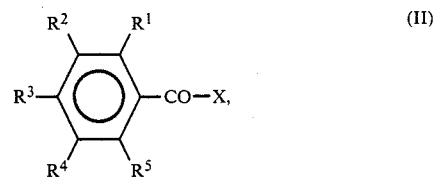

wherein $R^1$ to $R^5$ have the above-mentioned meaning and X as a monovalent moiety represents fluorine, chlorine or bromine and as a bivalent moiety the oxygen atom of an anhydride bridge, with a perfluoroalkyl halide of the general formula $C_nF_{2n+1}$-Hal (III), wherein Hal represents chlorine, bromine or iodine and n is an integer from 1 to 6, in the presence of a trisdialkyl amide of phosphorus acid of the general formula P[N(alkyl)2]3 (IV).

18 Claims, No Drawings

PROCESS FOR THE PREPARATION OF ARYL PERFLUOROALKYL KETONES

The invention relates to a process for the preparation of aryl perfluoroalkyl ketones by reaction of aromatic carboxylic acid derivatives with perfluoroalkyl halides in the presence of phosphorous acid triamides.

Aryl perfluoroalkyl ketones are important intermediates for the preparation of medicaments, plant protection agents and plastics. They can be produced by the two following general synthesis routes.

The reaction of perfluoroalkylcarboxylic acid halides with aromatics according to the manner of a Friedel-Crafts substitution yields the corresponding ketones (Tetrahedron 42, 547–552 (1986)). The position in which the perfluoroalkoxycarbonyl group is bonded to the aromatic ring is dependent on the nature and position of the substituents present so that in general only certain types of substituted aryl perfluoroalkyl ketones can be obtained using this process. Further disadvantages of this process are the possible formation of positional isomers in the substitution on the aryl ring, possible multiple substitution, restriction to activated aromatics and to certain substituents on the aromatic ring inasmuch as many substituents react with the Friedel-Crafts catalyst or form complexes and thus a further reaction in the desired sense is prevented.

It is furthermore known that aryl perfluoroalkyl ketones can be obtained by reaction of aryl organometallic compounds with perfluoroalkylcarboxylic acid derivatives or by the reversed process of a reaction of aromatic carboxylic acid derivatives with perfluoroalkyl organometallic compounds (J. Fluorine Chem. 18, 117-129 (1981); J. Am. Chem. Soc. 78, 2268–2270 (1956); Bull. Chem. Soc. Jap. 48, 1339–40 (1975)). In this connection, organometallic compounds of base metals, which are usually prepared from the corresponding aryl halides or perfluoroalkyl halides and a metal, such as magnesium, lithium or sodium, are used.

As a rule, complicated preparation and the lability of the organometallic compounds to be prepared first are disadvantageous here. In the most frequently carried out generally utilizable process for the preparation of aryl perfluoroalkyl ketones according to literature information, 3 moles of aryl organometallic compound are required per mole of perfluoroalkylcarboxylic acid and in addition often only unsatisfactory yields are obtained (J. Fluorine Chem. 18, 323–29 (1981)).

The invention now relates to a simple, one-step process for the preparation of aryl perfluoroalkyl ketones from aromatic carboxylic acid derivatives with the avoidance of the preparation and use of the previously mentioned organometallic compounds.

It has now been found that arylcarboxylic acid derivatives of the general formula II

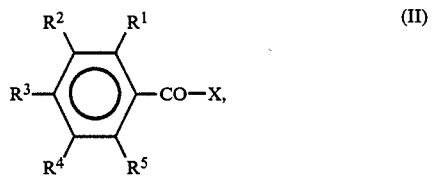

(see patent claim 1), in which X as a univalent symbol denotes chlorine, bromine or fluorine and as a divalent symbol denotes the anhydride bridge, can be reacted with perfluoroalkyl halides of the general formula $C_nF_{2n+1}$-Hal (III) in which Hal is chlorine, bromine or iodine, even in the presence of phosphorous acid trisdialkylamides (in other words tris(dialkylamino)phosphines) of the general formula $P(N(alkyl)_2)_3$ (IV) to give the desired aryl perfluoroalkyl ketones of the general formula I

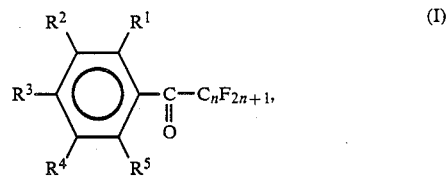

(see patent claim 1). In the formulae I and II, the radicals $R^1$ to $R^5$ represent hydrogen or have the meaning indicated further below.

The process according to the invention not only has the advantage of simplicity, but also that the starting materials are easily accessible. The yields are in many cases clearly higher than the corresponding literature information for the ketones prepared by other methods.

The halides (X=chlorine, bromine or fluorine), or also corresponding anhydrides of the aromatic carboxylic acids can be employed as aromatic carboxylic acid derivatives (II); the carboxylic acid chlorides and fluorides, which are also most accessible as a rule, are preferred. The aromatic carboxylic acid derivatives can be unsubstituted or can carry one or more identical or different substituents $R^1$ to $R^5$ having a meaning other than hydrogen. Suitable substituents are, for example, alkyl, alkoxy and alkylthio radicals each having 1 to 6, in particular 1 to 3, carbon atoms, where the alkyl radicals can be perfluorinated, and also halogen (fluorine, chlorine, bromine and iodine). Expediently, not more than three and preferably at most two substituents $R^1$ to $R^5$ having a meaning other than hydrogen are bonded to the aromatic ring. The alkyl, alkoxy and alkylthio substituents expediently together contain at most 4 carbon atoms and can be straight-chain or branched.

In general, compounds having 1 to 6, in particular 1 to 3, carbon atoms are used as perfluoroalkyl halides which can be straight-chain or branched, preferably $CF_3Br$ and the homologous perfluoroalkyl iodides of the general formula $C_nF_{2n+1}I$ having n=1 to 6 or up to 3.

Suitable phosphorous acid trisdialkylamides (IV) are primarily the lower alkyl compounds, in particular those having $C_1$–$C_4$-alkyl, such as trisdimethylaminophosphine, trisdiethylaminophosphine and trisdipropyl- or isopropylaminophosphine; preferably trisdiethylaminophosphine $P(N(CH_2CH_3)_2)_3$ is used. This can be produced very simply in high yields by reaction of phosphorus trichloride with diethylamine in a solvent which is inert towards the reaction participants, for example an aliphatic, cycloaliphatic or aromatic hydrocarbon or a hydrocarbon mixture. The dialkylamino groups can contain identical or different alkyl groups.

In the reaction of the arylcarboxylic acid halide with a perfluoroalkyl halide under the influence of the phosphorous acid trisdialkylamide, formally one mole of halogen or mixed halogen is eliminated and a salt-like adduct is formed from the phosphorous acid triamide, and halogen and also an aryl perfluoroalkyl ketone are formed.

The reaction of arylcarboxylic acid halide with perfluoroalkyl halide in the presence of phosphorous acid triamide is in general carried out at temperatures from about −100° C. to +40° C. The short-chain perfluoroalkyl halides mostly react very rapidly at −78° C. In the perfluoroalkyl halides having at least 2 carbon atoms, it is often necessary to increase the reaction temperatures in order to achieve a rapid reaction; temperatures above −40° C. and, for example, up to +20° C. are then preferred. The duration of the reaction is known to be dependent on the other conditions, in particular the reaction temperature. The reaction is in general complete within a period from a few minutes up to several hours.

The reactions are in general carried out without use of overpressure. However, it can be expedient in individual cases, for example in the reaction of perfluoromethyl halides, to also work at elevated pressure, primarily if the reaction is carried out above the boiling temperature (at atmospheric pressure) of the perfluoroalkyl halide. In practice, the reaction is thus then carried out at least at the intrinsic pressure.

The present process is expediently carried out under anhydrous conditions in the presence of a solvent or diluent which is inert towards the reaction participants. Those which are primarily employed are aprotic liquids. For example, halogenated hydrocarbons such as methylene chloride, tetrachloroethane, nitriles, for example acetonitrile or its homologs or benzonitrile, esters such as diethyl carbonate or ethylene carbonate and ethers such as tetrahydrofuran or dimethoxyethane are used. The solvent should be as anhydrous as possible.

During the total duration of the reaction, it is advantageous, for example by stirring, to provide good intermixing of the batch and also to keep the salt-like intermediates and attendant products in solution by selection of a suitable solvent.

The reagents are used in an amount at least equivalent to the aromatic carboxylic acid derivative, often in an excess of, for example, 2% to 20%.

The nature and the order of the combination of the three components is variable. The process according to the invention can, for example, be carried out so that solvent, carboxylic acid halide and perfluoroalkyl halide are initially introduced and the phosphorous acid triamide is metered in. All components can also be combined simultaneously.

The working up of the reaction mixture advantageously takes place by distillative separation of the components. It is often also expedient to separate off the resulting aryl perfluoroalkyl ketone from the simultaneously resulting phosphorous acid triamide/halogen adduct (in other words a phosphonium salt) by an extraction. In the case of an addition of a non-polar solvent, for example a hydrocarbon such as hexane, to the reaction mixture, two phases are obtained, the perfluoroalkyl compound being in the upper phase and the lower phase essentially containing the phosphonium salt as an attendant product and which is insoluble in the hydrocarbon.

EXAMPLES (1) Under protective gas, 41 g (0.27 mol) of trifluoromethyl bromide are condensed into a solution of 42 g (0.25 mol) of 3,4-dimethylbenzoyl chloride in 150 ml of $CH_2Cl_2$ in a round-bottomed flask at about −70° C. A solution of 66.7 g (0.27 mol) of phosphorous acid trisdiethylamide in 50 ml of $CH_2Cl_2$ are then metered in at about −70° C., the first 90% of the solution being added rapidly and the last 10% of the solution being metered in slowly (during the course of about 2 hours). The mixture is subsequently stirred for one hour more at this temperature and then warmed to room temperature. After addition of the same volume of hexane, 2 phases are formed. After phase separation, the lower phase is carefully extracted using hexane; the combined hexane phases are concentrated and distilled under reduced pressure. 20.8 g (41% yield) of 1-(3,4-dimethylphenyl)-2,2,2-trifluoroethan-1-one of b.p. 98°–99° C./22 mbar are obtained.

(2) Under protective gas, 39 g (0.25 mol) of m-toluoyl chloride in 150 ml of $CH_2Cl_2$ are initially introduced at about −20° C. into a round-bottomed flask. 67 g (0.27 mol) of pentafluoroethyl iodide are first condensed in and 66.7 g (0.27 mol) of phosphorous acid trisdiethylamide are then metered in. The reaction mixture is subsequently stirred for 5 more hours at 0° C.

Working up analogously to Example 1 yields 33.2 g (56% yield) of 1-(3-methylphenyl)-2,2,3,3,3-pentafluoropropan1-one of b.p. 75°–78° C./12 mbar.

(3) Under protective gas, 31.5 g (0.185 mol) of 3-methoxybenzoyl chloride in 150 ml of $CH_2Cl_2$ are initially introduced into a round-bottomed flask. 48.6 g (0.2 mol) of phosphorous acid trisdiethylamide are added at about −10° C. 50 g (0.2 mol) of pentafluoroethyl iodide are then introduced into the reaction mixture at 0° C. during the course of one hour. The mixture is stirred for a further 5 hours at 0° C. and then worked up analogously to Example 1. 22.9 g (61% yield) of 1-(3-methoxyphenyl)-2,2,3,3,3-pentafluoropropan-1-one of b.p. 95°–97° C./11 mbar are obtained.

(4) Under protective gas, 22 g (0.18 mol) of benzoyl fluoride and 55.3 g (0.18 mol) of perfluoroisopropyl iodide in 150 ml of $CH_2Cl_2$ are initially introduced into a round-bottomed flask. 45 g (0.18 mol) of phosphorous acid trisdiethylamide are added dropwise at about −70° C. The mixture is stirred for 12 hours at −70° C. and, after warming, worked up analogously to Example 1. 38.5 g (78%) of 1-phenyl-2,3,3,3-tetrafluoro-2-trifluoromethyl-propan-1-one of b.p. 90°–92° C./80 mbar are obtained.

(5) Under protective gas, 27.3 g (0.16 mol) of p-methoxybenzoyl chloride and 53.3 g (0.18 mol) of perfluoroisopropyl iodide in 150 ml of $CH_2Cl_2$ are initially introduced into a round-bottomed flask. 45 g (0.18 mol) of phosphorous acid trisdiethylamide are metered in at about −20° C. during the course of 3 hours. The mixture is subsequently stirred at about −10° C. for 5 hours and, after warming, worked up analogously to Example 1. 37 g (76%) of 1-(4-methoxyphenyl)-2,3,3,3-tetrafluoro-2-trifluoromethylpropan-1-one of b.p. 97°–99° C./10 mbar are obtained.

(6) Under protective gas, 35 g (0.25 mol) of benzoyl chloride in 150 ml of $CH_2Cl_2$ are initially introduced at about −20° C. into a round-bottomed flask. 67 g (0.27 mol) of pentafluoroethyl iodide are first condensed in and 66.7 g (0.27 mol) of phosphorous acid trisdiethylamide are then metered in. The reaction mixture is subsequently stirred at 0° C. for 5 hours more. After addition of the same volume of hexane to the reaction mixture, 2 phases are formed. After phase separation, the lower phase is carefully extracted using hexane; the combined hexane phases are concentrated and distilled under reduced pressure. 20.8 g (58% yield) of pentafluoroethyl phenyl ketone of b.p. 76–77/40 mbar are obtained.

(7) to (16) The preparation of the following compounds can be seen from the table below, where R represents the radical or radicals $R^1$ to $R^5$ of the formula I indicated. In Example 16, the reaction was carried out analogously to Example 2, but with the additional variation that acetonitrile was used as the solvent instead of dichloromethane.

| Example | R | $R_F$ | Yield | b.p. °C./mbar | Process analogous to Example |
|---|---|---|---|---|---|
| 7 | H | $CF_3$ | 52% | 84–85/80 | 1 |
| 8 | 3-$CH_3$ | $CF_3$ | 48% | 75–76/20 | 1 |
| 9 | 4-$CH_3$ | $C_2F_5$ | 58% | 82–83/10 | 2 |
| 10 | 3,5(O$CH_3$)$_2$ | $C_2F_5$ | 44% | 73–74/0,2 | 2 |
| 11 | 2-Cl | $C_3F_7$ | 83% | 76–77/7 | 4 |
| 12 | 4-Cl | $C_2F_5$ | 42% | 88–89/10 | 2 |
| 13 | 3-F | $C_3F_7$ | 81% | 70–71/20 | 4 |
| 14 | 3-F | $C_2F_5$ | 21% | 95–97/90 | 2 |
| 15 | 4-$CF_3$ | $C_2F_5$ | 42% | 86–87/20 | 2 |
| 16 | 3-$CH_3$ | $C_2F_5$ | 44% | 78–79/9 | 2 |

We claim:

1. A process for the preparation of arylperfluoroalkyl ketones of the general formula I

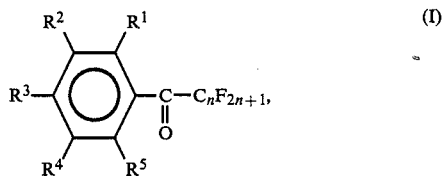

wherein $R^1$ to $R^5$ represent at least one of the substituents hydrogen, halogen, alkyl, alkoxy, alkylthio and perfluorinated alkyl, each having from 1 to 6 carbon atoms and n is an integer from 1 to 6, which comprises reacting an aryl carbonyl compound having the general formula II

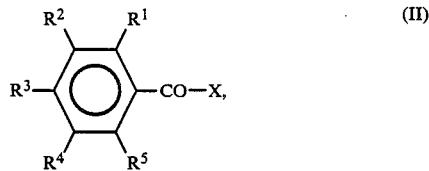

wherein $R^1$ to $R^5$ have the above-mentioned meaning and X as a monovalent moiety represents fluorine, chlorine or bromine and as a bivalent moiety the oxygen atom of an anhydride bridge, with a perfluoroalkyl halide of the general formula $C_nF_{2n+1}$-Hal (III), wherein Hal represents chlorine, bromine or iodine and n is an integer from 1 to 6, in the presence of a trisdialkyl amide of phosphorous acid of the general formula P[N(alkyl)$_2$]$_3$ (IV).

2. A process as claimed in claim 1, wherein at most three of the substituents $R^1$ to $R^5$ have a meaning other than hydrogen.

3. A process as claimed in claim 2, wherein at most two of the substituents $R^1$ to $R^5$ have a meaning other than hydrogen.

4. A process as claimed in claim 1, wherein the substituents $R^1$ to $R^5$ contain altogether at most 4 carbon atoms.

5. A process as claimed in claim 1, wherein X represents fluorine or chlorine.

6. A process as claimed in claim 1, wherein the perfluoroalkyl halide III has from 1 to 3 carbon atoms.

7. A process as claimed in claim 6, wherein the perfluoroalkyl halide is $CF_3Br$.

8. A process as claimed in claim 1, wherein a perfluoroalkyl iodide is reacted.

9. A process as claimed in claim 1, wherein each alkyl in compound IV has from 1 to 4 carbon atoms.

10. A process as claimed in claim 9, wherein the trisdialkyl amide of phosphorous acid has the formula P[N($CH_2CH_3$)$_2$]$_3$.

11. A process as claimed in claim 1, wherein the reaction is carried out at a temperature in the range of from $-100°$ C. to $+40°$ C.

12. A process as claimed in claim 11, wherein a perfluoroalkyl halide of at least 2 carbon atoms is reacted at a temperature above $-40°$ C.

13. A process as claimed in claim 12, wherein the reaction temperature is at most $+20°$ C.

14. A process as claimed in claim 1, which is carried out at a pressure not exceeding ambient pressure.

15. A process as claimed in claim 1, wherein a perfluoromethyl halide is reacted at a pressure higher than ambient pressure.

16. A process as claimed in claim 1, which is carried out under anhydrous conditions in the presence of a solvent or diluent inert towards the reactants.

17. A process as claimed in claim 16, wherein the solvent or diluent is an aprotic liquid.

18. A process as claimed in claim 1, wherein the perfluoroalkyl halide III and the trisdialkylamide of the phosphorous acid P[N(alkyl)$_2$]$_3$ IV are applied in an amount at least equivalent to the aryl carbonyl compound II, and at most in an amount of 20% above the equivalent amount.

* * * * *